United States Patent [19]
Kestler

[11] Patent Number: 5,003,972
[45] Date of Patent: Apr. 2, 1991

[54] ATHLETIC SUPPORTER

[76] Inventor: Jeffrey L. Kestler, 249 Long Hill Dr., Morris County, N.J. 07078

[21] Appl. No.: 333,725

[22] Filed: Apr. 3, 1989

Related U.S. Application Data

[63] Continuation of Ser. No. 114,220, Oct. 28, 1987, abandoned.

[51] Int. Cl.5 .............................................. A41B 9/12
[52] U.S. Cl. .................................. 128/158; 128/171; 128/161; 128/162; 128/159; 128/100.1
[58] Field of Search ................................ 128/100, 171

[56] References Cited

U.S. PATENT DOCUMENTS

| | | | |
|---|---|---|---|
| 286,657 | 10/1883 | Ware | 128/158 |
| 628,392 | 7/1899 | Cooper . | |
| 1,030,224 | 6/1912 | Bauer . | |
| 1,052,765 | 2/1913 | Strauss | 128/159 |
| 1,313,165 | 8/1919 | Casselman | 128/158 |
| 1,560,753 | 11/1925 | Young . | |
| 2,293,998 | 8/1942 | Norwood | 128/158 X |
| 3,335,721 | 8/1967 | Gastwirth | 128/171 |
| 3,504,671 | 4/1970 | Nelkin | 128/158 |
| 3,518,995 | 7/1970 | Claff | 128/158 |
| 3,547,117 | 12/1970 | Smithers . | |
| 3,782,375 | 1/1974 | Donars | 128/158 |
| 4,122,849 | 10/1978 | Dietz | 128/161 |
| 4,141,357 | 2/1979 | Dietz . | |
| 4,590,931 | 5/1986 | Kidwell | 128/158 |

FOREIGN PATENT DOCUMENTS 0295262  8/1928  United Kingdom .

Primary Examiner—V. Millin

[57] ABSTRACT

An athletic supporter provides enhanced support and comfort by employing an attachment means between the pouch and waistband. This attachment means provides a plurality of position for attachment that allows the support to be adjusted to the situation.

6 Claims, 3 Drawing Sheets

ATHLETIC SUPPORTER

This application is a continuation of application Ser. No. 114,220, filed on Oct. 28, 1987, which is hereby incorporated by reference is abandoned.

BACKGROUND OF THE INVENTION

1. Field of the Invention

This invention relates to athletic equipment and in particular athletic supporters.

2. Art Background

The avowed purpose for athletic supporters is the support of the genitals and scrotum during athletic endeavors or during less strenuous activities. The supporters generally include a waistband, a downward and then rearward projecting pouch appended to the front of the waistband to support the scrotum and genitals and a pair of straps extending from the bottom of the pouch to separated positions on the waistband. Supporters are made in a few discrete sizes. However this concept of a few sizes fitting all is often unsatisfactory. Even if a generically sized supporter fits when new, lending some of the desired support, washings and use soon take their toll.

Attempts to extend the usefulness of supporters have often involved improvement of the materials, e.g., elastic materials. Some other approaches involve mechanical expedients. For example, U.S. Pat. No. 3,547,117, issued Dec. 15, 1970, describes an adjustable waistband having a fastener, e.g., a Velcro ® fastener, to reduce or enlarge the circumference of the waistband. This adjustability does not significantly improve the support provided. An alternate approach to increased convenience (U.S. Pat. No. 4,141,357, issued Feb. 27, 1979) employs, as shown in FIG. 1, a pouch, 1, with no straps at the bottom of the pouch but having two adjustable straps, 3 and 4, attached to opposing ends at the top of the pouch and adapted to attach to the waistband of a separate garment, e.g., a bathing suit. Lack of straps at the bottom of the pouch significantly decreases support.

Attempts to compensate for the varying degrees of support required for different activities for the variety of human configurations and for the ranges of use have not been entirely successful.

SUMMARY OF THE INVENTION

Significant support for a wide variety of physiques and activities as well as compensation for the effects of wear is possible with the inventive supporter configuration. In particular a configuration is used that includes: (1) a waistband, (2) a pouch attachable to the waistband in the front, (3) means for attaching the pouch to the waistband, and (4) holding members extending from the bottom portion of the pouch to the waistband. The means for attachment should satisfy certain criteria. The attachment means should provide for attachment and detachment from a plurality of positions extending in a direction from the bottom of the waistband to the top. The attachment at each such position should be such that (1) the pouch should advantageously not substantially distort downwardly due to the forces exerted upon attachment by contact with the wearer's body and such that (2) the waistband should not substantially pucker due to the forces upon attachment exerted by contact with the body.

For example, excellent support for a wide variety of body configurations is achieved by employing a hook and loop attachment means such as Velcro ®. In one specific embodiment one portion of the attachment means, e.g., the hooks, is arrayed substantially completely across the top of the pouch and the other portion of the attachment means, e.g., the loops, is arrayed across the waistband (37 in FIG. 2) width and extends along the circumference of the waistband a distance substantially corresponding to the dimension of the pouch occupied by the attachment means, e.g., the hooks. In this embodiment the support afforded is adjusted by pulling the top of the pouch upwardly and attaching it at a comfortable position on the waistband. The resulting support and comfort is substantially maintained because the pouch does not sag attachment is all across the top of the pouch) and the waistband does not pucker (the force generated by the desired support is distributed over a relatively substantial portion of the waistband).

DETAILED DESCRIPTION

Figure 1:
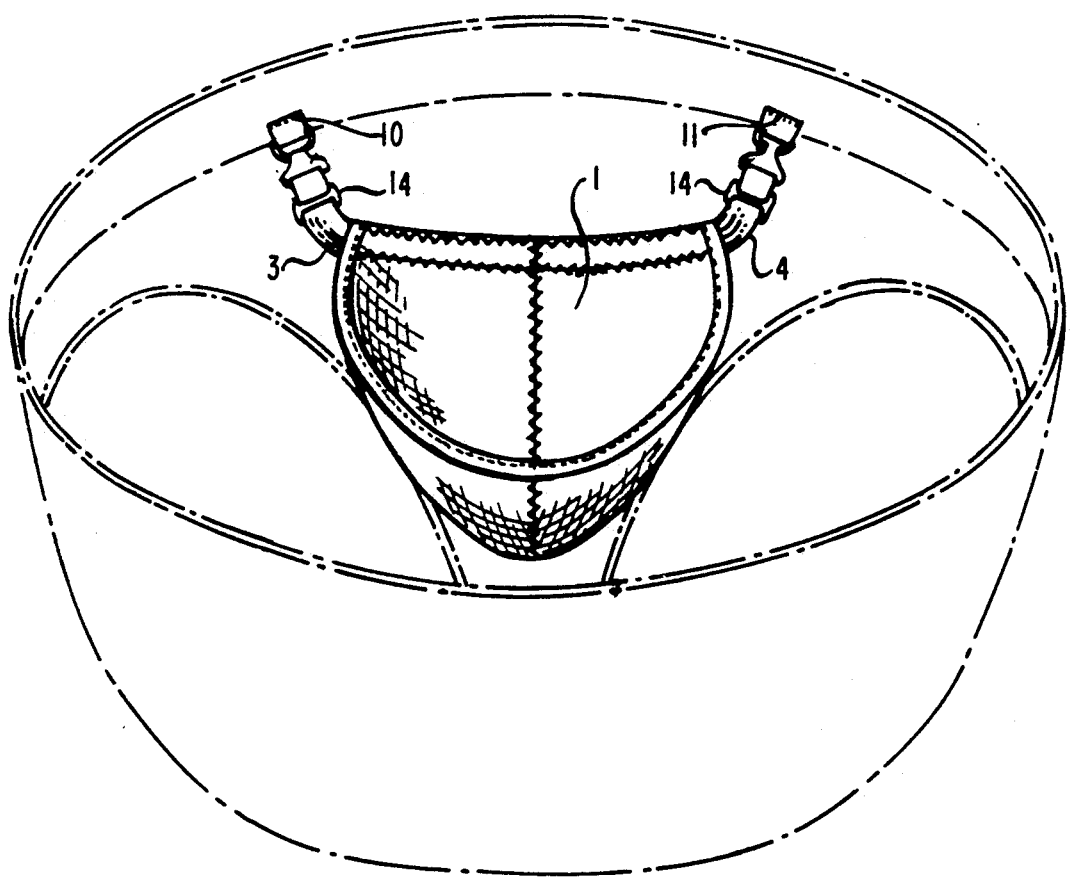
FIG. 1 is illustrative of embodiments outside the invention.

The inventive athletic supporters are characterized by their comfort and adjustable support. These attributes are obtained by employing (1) a waistband, 37 in FIGS. 2 and 3, (2) a pouch, 35, (3) an appropriate means for attaching the upper portion of the pouch to the front portion of the waistband, and (4) holding members, 33, that extend from and provide support for the bottom portion of the pouch while extending to the waistband. (The different elements of the athletic supporter need not be discrete. It is possible, for example, to form the waistband and holding members from one piece of cloth, e.g., a structure that resembles an underwear brief.)

The expedient employed to provide the means for attachment is not critical, but it is desirable that attachment and detachment be relatively convenient. Expedients such as a plurality of snaps, a plurality of hooks with eyes, and/or Velcro ® are suitable. However, the expedient should be configured so that certain criteria are satisfied. The attachment should provide a plurality of positions for attachment extending in a direction from the bottom, 36, of the waistband, i.e., the edge closest to the toes when the athletic supporter is worn, to the top. (The waistband need not be a constant width. For example, a larger range of adjustment is possible if the waistband is wider where the pouch is attached.) For example, snaps are provided in rows, e.g., rows 21, 22, 23, and 24 in FIG. 2 parallel to the bottom edge of the waistband, with a plurality of rows stacked in an upward direction. Each row corresponds to an attachment position for the pouch. In another embodiment, a Velcro ® patch 30 in FIG. 3 (either the hooks or the loops) extends along the waistband and also extends in the direction from bottom to top of the waistband. (Directions and locations such as upward, downward, bottom and top as used in this disclosure are those that apply when the athletic supporter is being worn and the wearer is standing on his feet.) In all embodiments, irrespective of the expedient utilized for attachment, a plurality of positions for attachment on the waistband and/or pouch is provided. (A position of waistband (pouch) attachment is a curve defining the lower boundary for the points of waistband (pouch) attachment.)

To obtain the entire benefit of comfort and adjustability it is desirable that the attachment means satisfy more than the requirement of multi-position attachment. The pouch should attach to the waistband so that upon pouch attachment the forces produced due to contact of the athletic supporter with the body (1) do not induce substantial puckering of the waistband and (2) do not produce a downward distortion of the imaginary curve connecting the uppermost points of the pouch before attachment that are no higher than the position of ultimate pouch attachment. Puckering in this context is a loss of contact of the waistband with the body in localized regions. Also in the context of the disclosure a point of attachment is a point (1) on the pouch and waistband of direct attachment, or (2) the point on the pouch (point of pouch attachment) and point on the waistband (point of waistband attachment) to which an intervening member connecting the two attaches.

Figure 2:
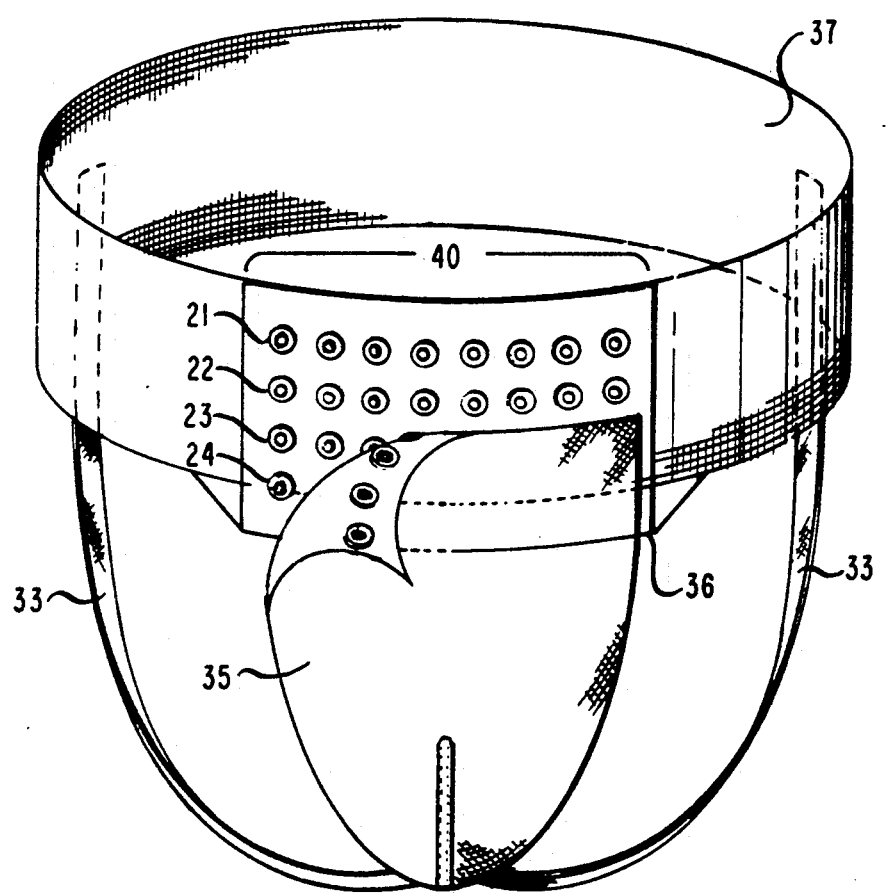
FIGS. 2 and 3 are illustrative of embodiments of the invention and of the manner in which the inventive athletic supporter provides comfort and adjustable support.
Figure 3:
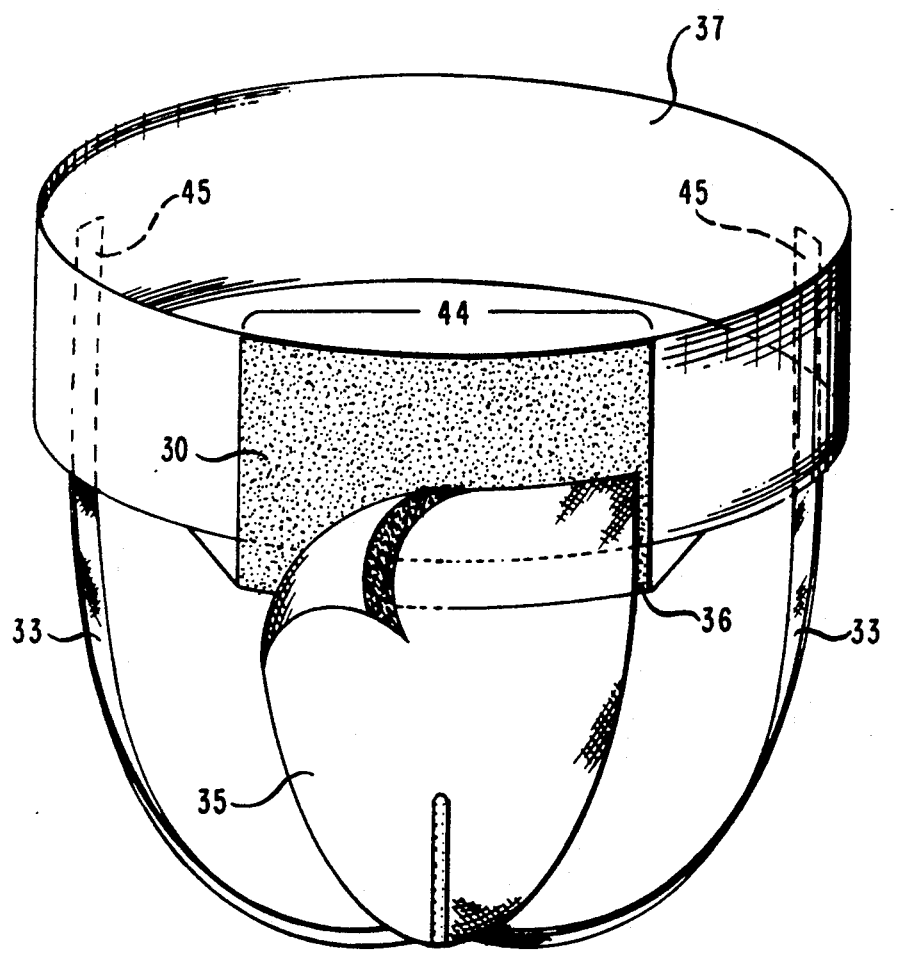

The embodiments of FIG. 2 and FIG. 3 satisfy these conditions. In FIG. 2 the snaps in a given row, for example 21, are sufficiently closely spaced so that substantial downward distortion of the pouch does not occur. Additionally, because the forces of contact with the body are spread over a relatively long region of the waistband (region 40 denoted by bracket) substantial puckering of the waistband is avoided.

Similarly, in the embodiments of FIG. 3, the forces are spread over the bracketed region 44 to avoid puckering and since the pouch is supported across its width substantial deformation is also avoided. (It is possible to attach the pouch to the waistband in a direction that is not parallel to the edge of the waistband.)

In contrast, for the athletic supporter shown in FIG. 1, as the adjustment is made forces are applied at points 10 and 11. Since the forces are not distributed there is a tendency for the waistband to pucker as the buckles, 14, are tightened to provide adjustment. Additionally the top of the pouch is supported only in the corners and thus sags in the middle. If more force is applied at the corners to remove the sag, this force is transferred to the waistband and contributes to puckering.

The use of, for example, a limited number of contact points, e.g., snaps, however is not to be totally precluded. Exemplary of the possibilities is the use of snaps on the pouch with stiffening members along the pouch and waistband. The stiffening member prevents sagging of the pouch and distributes forces to preclude puckering. Indeed, when Velcro ® is employed the fabric backing, when present, provides stiffening that contributes to the prevention of puckering.

The materials used for the pouch, means for attaching the pouch to the..waistband, and the waistband itself are not critical. Typically, materials such as stretchable cloth are used. The attaching members are generally sewn to the pouch and waistband. However, other means for connection are acceptable such as the use of Velcro ® that also provides adjustment. Additionally, it is possible for provision to be made for a hard cup or foam cushion such as used in contact sports. Adjustment such as where the support members attach to the waistband yields additional comfort especially when a hard cup is employed. The upward adjustment of the pouch puts tension on the supporting members. This tension is relieved by a concomitant adjustment of the supporting members such as at 45 in FIG. 3.

I claim:

1. A body comprising (1) a waistband, (2) a pouch, a substantial portion of which is stretchable, said pouch attachable to the front portion of said waistband, said pouch configured for supporting a scrotum and penis, and (3) a holding member extending from the bottom of said pouch to said waistband characterized in that said body includes a means for attaching said pouch to said waistband such that said means of attachment provides a plurality of positions attachment extending in the direction from the bottom to the top of said waistband and such that substantial pucker of said waistband and substantial sag of said pouch is avoided.

2. The body of claim 1 wherein said attachment means comprises a fabric having hooks combined with a fabric having loops.

3. The body of claim 2 wherein said holding member comprises two straps.

4. The body of claim 1 wherein said holding member comprises two straps.

5. The body of claim 1 wherein said pouch includes a hard cup or foam cushion.

6. The body of claim 1 wherein said waistband is wider in the front.

* * * * *